United States Patent [19]

Fritz

[11] Patent Number: 4,531,406
[45] Date of Patent: Jul. 30, 1985

[54] ULTRASONIC LIQUID QUANTITY MEASURING APPARATUS

[75] Inventor: Harold B. Fritz, Norcross, Ga.

[73] Assignee: Lockheed Corporation, Burbank, Calif.

[21] Appl. No.: 437,805

[22] Filed: Oct. 29, 1982

[51] Int. Cl.³ .............................................. G01S 15/08
[52] U.S. Cl. ..................................... 73/290 V; 73/644
[58] Field of Search ............ 73/290 V, 644; 367/108, 367/902, 908; 310/336, 328

[56] References Cited

U.S. PATENT DOCUMENTS

| | | | |
|---|---|---|---|
| 3,010,318 | 11/1961 | Mongan | 73/290 V |
| 3,184,969 | 5/1965 | Bolton | 73/290 V |
| 4,183,007 | 1/1980 | Baird | 367/908 |
| 4,229,798 | 10/1980 | Rosie | 73/290 V |
| 4,373,401 | 2/1983 | Baumoel | 73/644 |

FOREIGN PATENT DOCUMENTS 1150214  6/1963  Fed. Rep. of Germany .

*Primary Examiner*—Charles Frankfort
*Assistant Examiner*—Denis E. Corr
*Attorney, Agent, or Firm*—John J. Sullivan

[57] ABSTRACT

An ultrasonic liquid quantity measuring apparatus directs a collimated beam of ultrasonic energy from a transmitter transducer (14) through a conveyor (15) into the liquid (11) in a container (10) perpendicular to the top liquid surface. The ultrasonic beam travels with little loss through a tube (20) connected to the conveyor (15) until it reaches the top liquid surface. At this time the energy is reflected and detected with a receiver transducer (14). A microprocessor (34) measures the total signal round trip travel time representing the height of the liquid (11). Using several ultrasonic transducers (14) and knowing the size and shape of the container (10) the quantity of liquid (11) in the container (10) is accurately determined. A calibration (known reflected signal time) transducer (14a) is used to compensate for the change in propagation velocity due to temperature change in the liquid (11). Conventional electronic circuitry including the microprocessor (34) is employed to coordinate the operation of the several transducers (14 and 14a) automatically.

16 Claims, 6 Drawing Figures

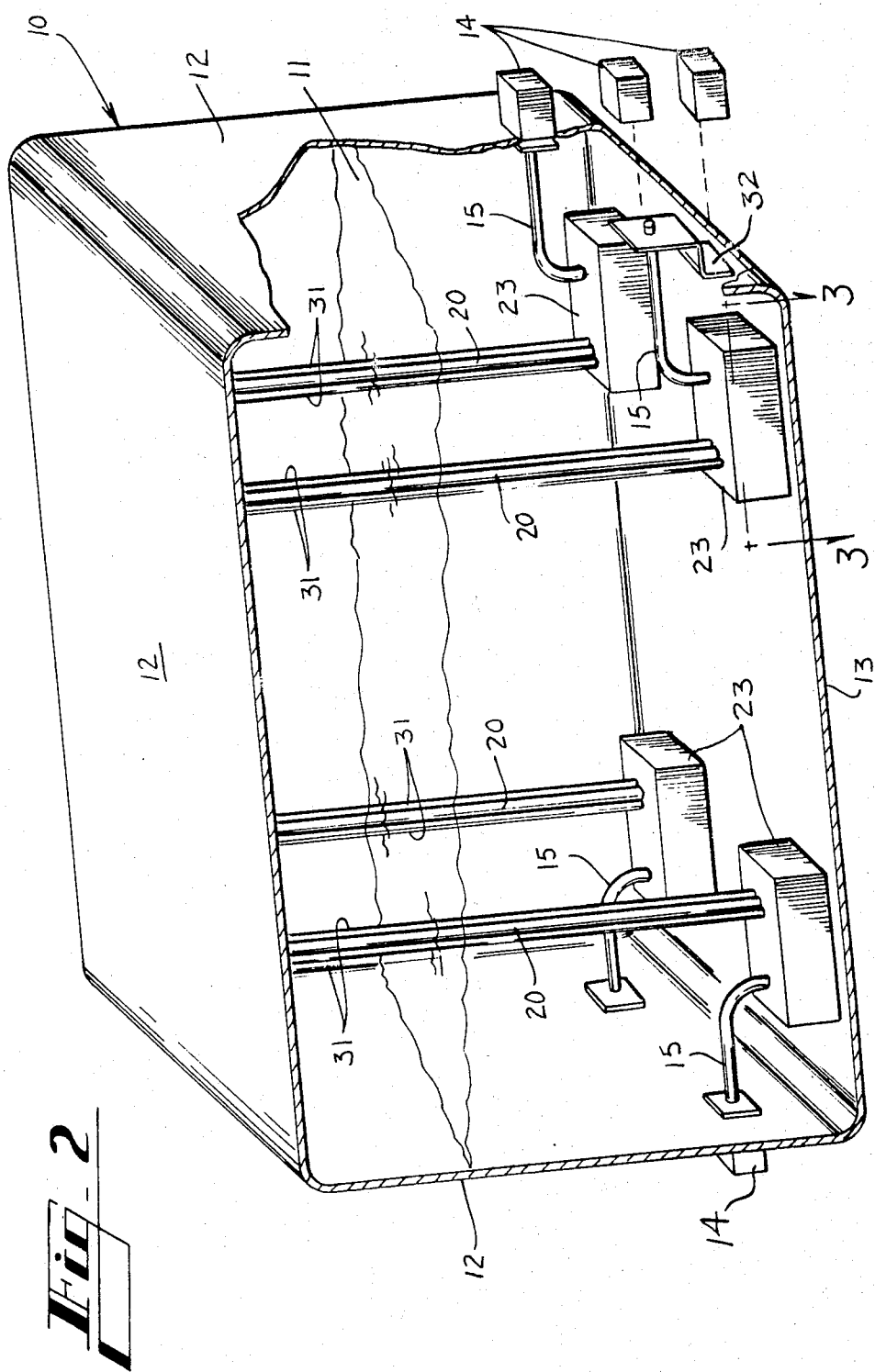

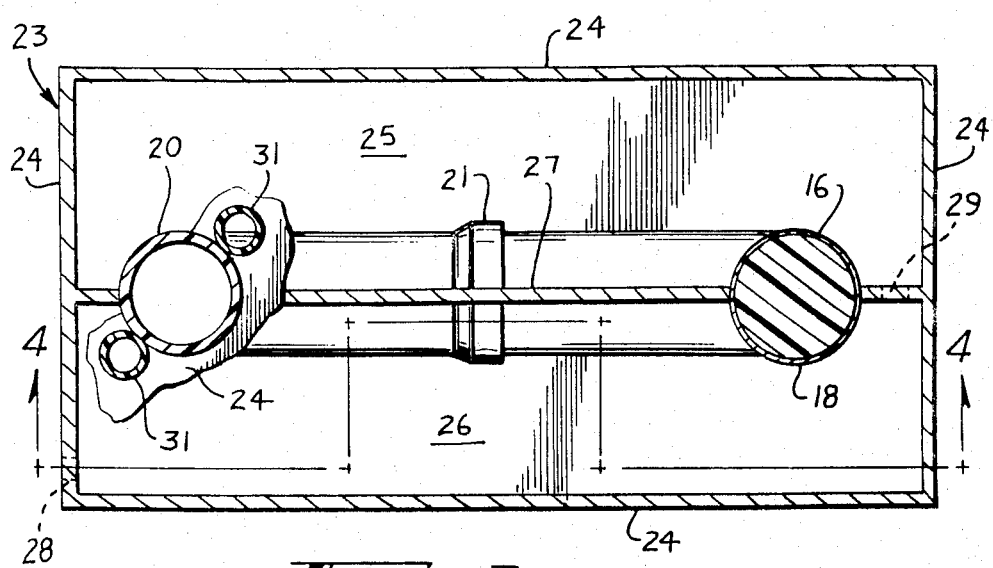
Fig_ 3
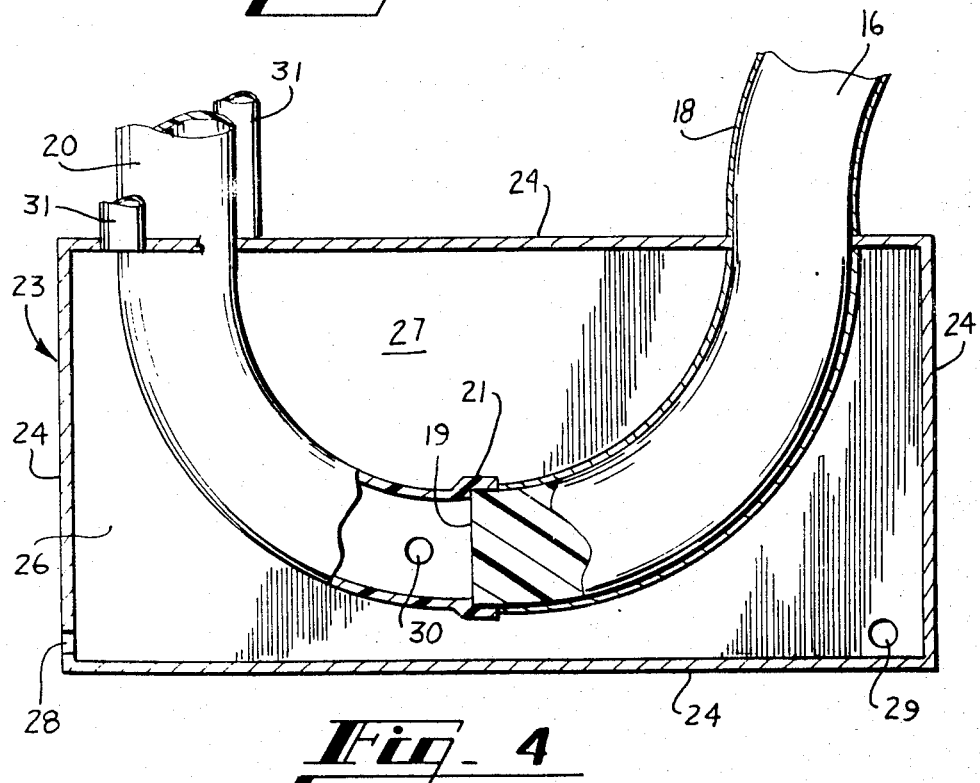
Fig_ 4

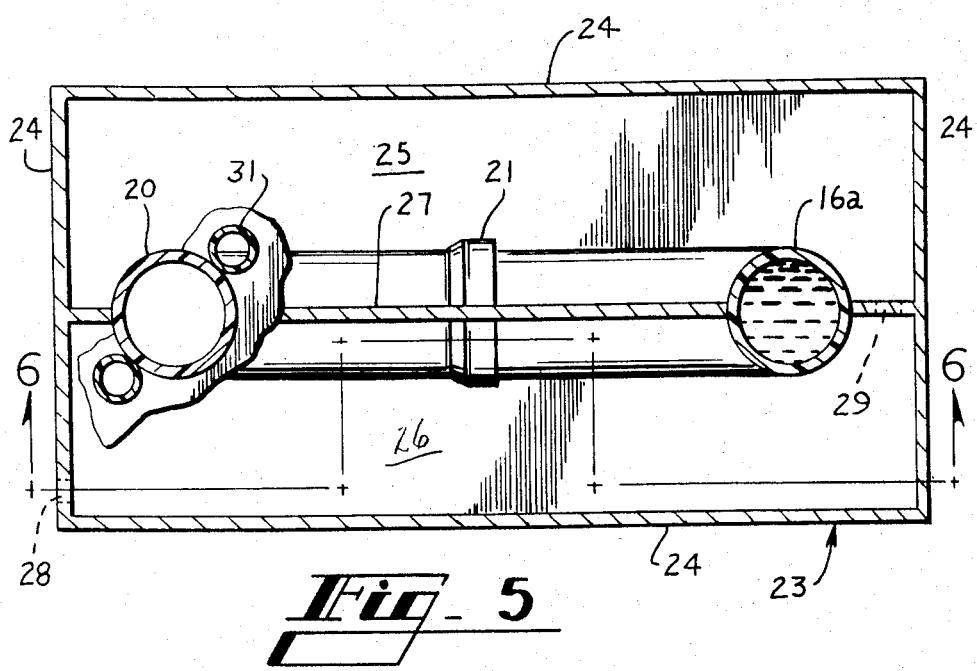
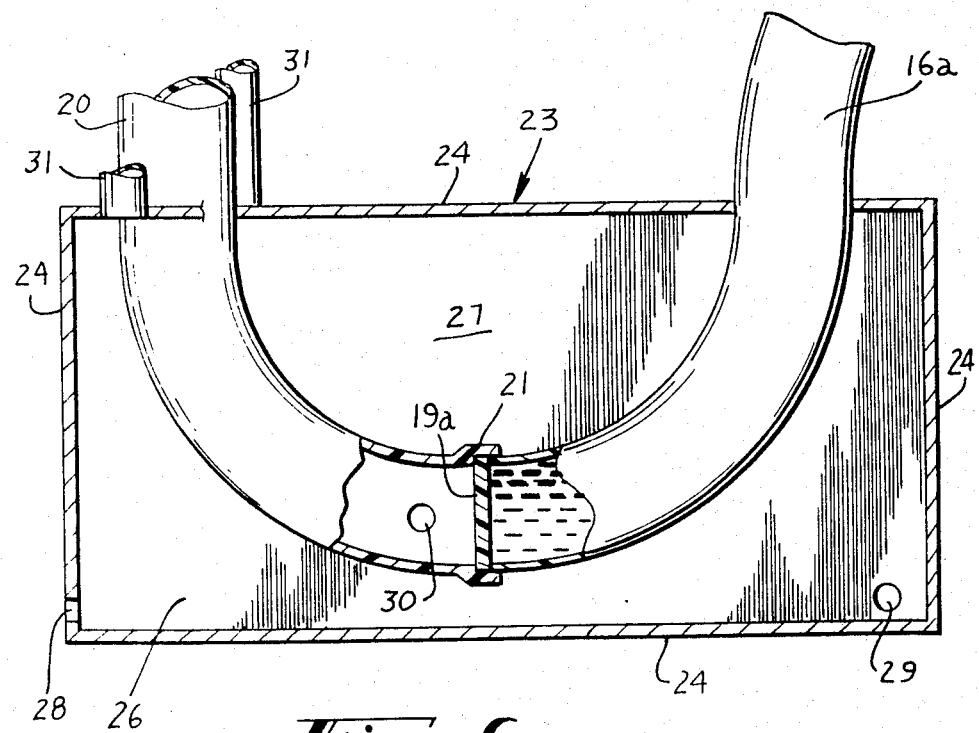

ULTRASONIC LIQUID QUANTITY MEASURING APPARATUS

TECHNICAL FIELD

This invention relates to measuring by ultrasonic techniques generally and more particularly to an ultrasonic liquid quantity measuring apparatus especially designed and adapted for operation in areas of limited accessibility and in hazardous environments.

In the measurement of liquid in containers it is desirable that an accurate reading of the quantity in the container is obtained. In addition, in the case of some containers, such as for example fuel tanks in aircraft, access is not easy. Also, and what is even more important, there exists the ever present risk of combustion and fire or explosion where fuel is involved.

BACKGROUND OF THE INVENTION

The common method presently used for fuel measurement in aircraft tanks employs a capacitance measuring technique in which two plates are mounted within the fuel tank. The fuel, being a dielectric between the plates, creates a varying capacitance as the quantity varies. To measure the capacitance, electrical energy is required to be applied to the plates which necessitates the use of electrical wiring into the tank. If a fault occurs within the capacitor plate assembly, or in the electrical wiring either inside or outside the tank from either the capacitance measuring system or other non-associated systems, such as a short circuit, a resulting high current could possibly flow in the short. This short can be produced by foreign material as small as a single filament of steel wool or by abrasion and shorting in the electrical wiring. These conditions within the tank result in a potentially hazardous, explosive condition. Results from fault analysis have shown that several amperes can flow through the shorted element if, for example, a standard laboratory multimeter such as a Simpson Model 260-5P is used to check the capacitance element and the multimeter is not properly connected. Moreover, corrective maintenance of the capacitance measuring system requires tank defueling, tank opening, tank purging and the entry of personnel in this hazardous environment together with the use of electrical troubleshooting apparatus. Several on-board aircraft fires are said to have been associated with the capacitance probe fuel quantity measurement system.

In applications involving less volatile liquids such as oil and the like mechanical floats with potentiometer movement are sometimes employed. Such mechanisms are unacceptable in the more dynamic cases of aircraft because of their unreliability due to continual motion and a resulting short life. As an alternate, hot wire devices have been proposed. In this system electrical energy is used to heat a fine wire partially submerged in the oil and the resistance is measured.

BACKGROUND ART

The present state-of-the-art in the technology area of the present invention is revealed in the following U.S. Pat. Nos.: 2,753,542 (issued to Rod et al on July 3, 1956), 2,775,748 (issued to Rod et al on Dec. 25, 1956), 2,960,678 (issued to Beard et al on Nov. 15, 1960), 3,100,885 (issued to Welkowitz et al on Aug. 13, 1963), 3,115,615 (issued to Saper on Dec. 24, 1963), 3,214,974 (issued to Altman et al on Nov. 2, 1965), 3,237,451 (issued to Haeff on Mar. 1, 1966), 3,357,245 (issued to Wolfrum on Dec. 12, 1967), 3,411,351 (issued to Schwartz on Nov. 19, 1968), 3,985,030 (issued to Charlton on Oct. 12, 1976), 4,210,969 (issued to Massa on July 1, 1980), 4,229,798 (issued to Rosie et al on Oct. 21, 1980).

Of the foregoing Welkowitz, Saper, Charlton and Rosie are considered to be most pertinent with respect to the apparatus herein proposed. These prior art combinations, however, fall far short of satisfying the needs for which the present invention is presented for reasons to become more apparent.

DISCLOSURE OF INVENTION

In accordance with the present invention ultrasonic fuel quantity measurement is made by directing a collimated beam of ultrasonic energy into the tank from one end thereof so as to be disposed substantially perpendicular to the top fuel surface. This beam is made to travel with little or no appreciable loss until it is intercepted by a discontinuity in the continuum, namely the top fuel surface. At the discontinuity, or fuel surface, the energy is reflected and detected. The total signal travel time is measured from the original transmit signal to the reception of the reflected signal. This total roundtrip time represents the height or depth of the fuel in the tank. Taking multiple such readings at different, spaced locations and knowing the mathematical shape of the tank, the fuel quantity can be accurately determined.

More specifically, an ultrasonic pulser/receiver is employed which is time controlled by a microprocessor. The microprocessor applies a timing pulse to the pulser circuitry. Upon receiving an initial timing pulse, the pulse circuit applies a pulse to a transducer that is externally located on the fuel tank. An ultrasonic signal is generated by the transducer and directed toward the top fuel surface as a collimated beam of energy. When reflected either upward or downward from the top of the fuel surface, this beam is then detected by the same transducer. Using multiple such transducers at selected scattered locations around the tank the upper liquid surface plane can be determined. Once the plane of the liquid surface is known within a mathematically defined tank the liquid quantity can readily be calculated.

In those applications as envisioned by this invention where it is desirable not to physically place the transducer at the top or bottom of the liquid container as in the case of a fuel tank internally of an airplane wing, it is herein proposed to incorporate an ultrasonic signal conveying apparatus to operatively connect a remote transducer to an ultrasonic window or focusing "lens" adjacent the selected wall of the tank whereby signals are reflected accordingly relative to the top liquid surface.

By installing more than one transducer in a fuel tank and knowing the shape of the tank, the fuel quantity is calculated for different conditions of flight attitude. Also by using another transducer as a "standard" with known, reflected, signal-travel distance, the calculated fuel quantity can be corrected for variations due to temperature change.

Since the ultrasonic technique described herein employs only stationary mechanical elements within the tank or in contact with the fuel, it can be safely used in a hazardous, explosive environment, such as a fuel tank with volatile contents. The use of non-functional elements inside the tank, together with all functioning transducers and electric wires outside the tank eliminates the need for tank entry by personnel for maintenance purposes. Faults within this system or from non-associated systems will not create a hazard since all wire is external to the tank.

BRIEF DESCRIPTION OF DRAWINGS

With the above and other objects in view as will be apparent, this invention consists in the construction, combination and arrangement of parts all as hereinafter more fully described, claimed and illustrated in the accompanying drawings wherein:

FIG. 2 is a perspective view of the fuel tank of FIG. 1 along and the association of multiple transducers of the present apparatus therewith whereby the liquid quantity in the tank may be measured when the attitude of the tank is such as to dispose the liquid therein at an angle in both axes;

FIG. 3 is a section taken along line 3—3 of FIG. 2 to show the construction of one preferred ultrasonic signal conveying apparatus within the tank;

FIG. 4 is a section taken along line 4—4 of FIG. 3;

FIG. 5 is a section similar to FIG. 3 showing the construction of another preferred ultrasonic signal conveying apparatus within the tank; and FIG. 6 is a section taken along the line 6—6 of FIG. 5.

DETAILED DESCRIPTION AND STRUCTURE OF THE PREFERRED EMBODIMENTS

Figure 1:
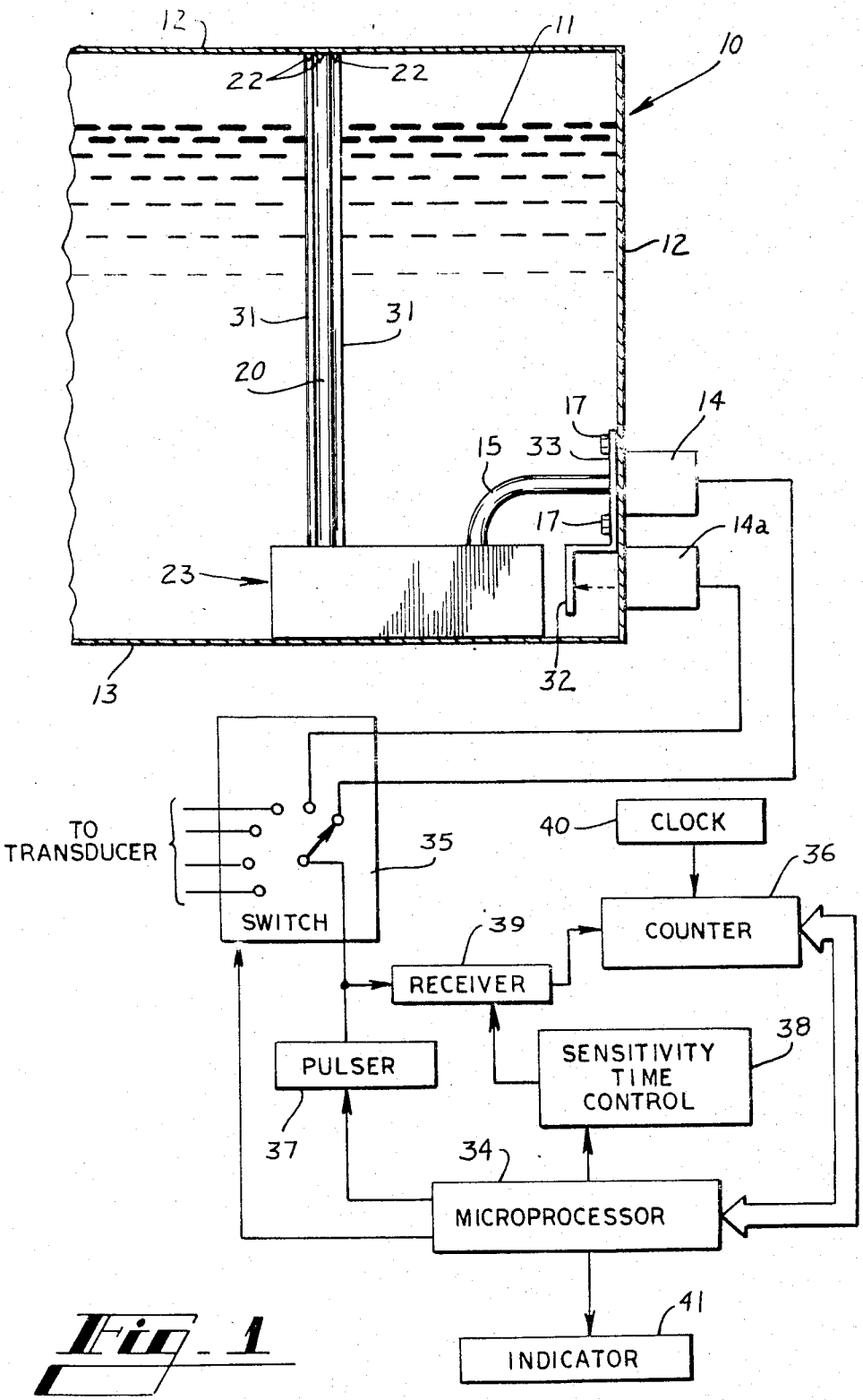
FIG. 1 is a section taken through a portion of a typical fuel tank for example within an airplane component to show generally an apparatus designed and constructed in accordance with the teachings hereof as applied thereto and an electronic block diagram of the control mechanism for the operation of such apparatus.

Referring more particularly to the drawings 10 designates a tank such as carried internally of an aircraft component in which fuel 11 in liquid form is stored. Such tanks 10 are of different shapes usually conforming with the shape of the particular aircraft components which house them. For the sake of simplicity a tank 10 is illustrated herein as generally rectangular being defined by top and side walls 12 and a bottom wall 13 which may be common with the adjacent aircraft component structure.

A predetermined number of ultrasonic transducers 14, such as for example piezoelectric or the like are mounted in any suitable manner to the side walls 12 externally of the tank 10, one disposed at each of a selected number of locations, herein illustrated for example as four. Each such transducer 14 when energized sends ultrasonic signals into a conveyor 15 which passes through the adjacent tank wall 12. This conveyor 15 is designed and adapted to have low ultrasonic propagation loss properties with a stable dielectric constant and may be in the form of either a rod 16 or a conduit 16a mounted to the surface of the adjacent wall 12 inside the tank 10. Each such rod 16 or conduit 16a is secured to the associated wall 12 by suitable, conventional means indicated generally at 17 and is shaped or bent as required by the particular tank 10 construction and location so as to direct and control the path of such signals.

Referring to FIGS. 3 and 4 the rod 16 is made of Rexolite 1422 which is the trade name of a proprietary material of C-LEC Plastics, Inc. 1717 Bridgeboro Road R. D. 1, Beverly, N.J. 08010 or the equivalent. Essentially, Rexolite 1422 is a thermoset cross-linked styrene copolymer having a combination of good physical and excellent electrical properties including low ultrasonic propagation loss and a stable dielectric constant which make it suitable for use in microwave lenses as well as for precision components. This rod 16 is metallic coated such as with chrome plate 18 which serves to contain the ultrasonic signals within the rod 16. Ideally the rod 16 and associated transducer 14 are located as near to the wall, e.g. the bottom 13, of the tank 10 as possible requiring a minimum of rod length and bending. However, in many cases the structure of the tank 10 and/or the associated aircraft structure does not permit this, requiring shaping such as for example that illustrated.

In any event the rod 16 terminates in an end 19 located adjacent the bottom of the tank 10. A conduit or tube 20 mates with the rod end 19 being secured therewith in any conventional manner such as by press fit facilitated by an enlarged or bell terminal 21 on the tube 20 which extends from the terminal 21 in a substantially vertical direction to the top wall 12 of the tank 10. Any conventional means may be employed to secure the tube 20 to the tank top wall 12 where an air vent hole or holes 22 (FIG. 1) are provided.

Referring to FIGS. 5 and 6 the conduit 16a, as an alternate to the rod 16 just described, is preferably made of metal filled with a low ultrasonic propagation loss material such as oil, silicone, grease, or the like, preferably a liquid as illustrated, being closed at each end by a diaphram or seal 19a which may be made of a polystyrene such as Rexolite 1422. The conduit 16a connects as for example by press-fit into the bell terminal 21 or tube 20 which as described extends in a substantially vertical direction to the top wall 12 of the tank 10.

In all other respects the arrangements illustrated in FIGS. 3 and 4 are identical to those in FIGS. 5 and 6. The portion of the conveyor 15 in either form 16 or 16a in the area of the tank bottom is made to pass through a trough 23 anchored in some appropriate manner to the bottom tank wall 13. Each trough 23 is totally enclosed on all sides, top and bottom by walls 24 and is composed of two internal chambers 25 and 26 separated by a center wall 27. A liquid vent hole 28 is provided in one wall 24 of the trough 23 adjacent the bottom thereof to permit fuel 11 within the tank 10 to enter chamber 26. A similar hole 29 is provided in the center wall 27 at the end thereof most remote from the hole 28 for the free passage of fuel 11 between the chambers 25 and 26.

The conveyor 15, either rod 16/tube 20 or conduit 16a/tube 20, on both sides of the connection 21 passes through the top wall 24 of the trough 23 and is made to straddle the center wall 27. Adjacent the connection 21 the wall of the tube 20 is pierced by a hole 30 for the free flow of fuel 11 in the chamber 25 into the tube 20.

Secured to the top wall 24 of the trough 23 on each side of the tube 20 so as to communicate with the interior of the trough 23 is a vent tube 31. Each vent tube 31 extends vertically to the top tank wall 12 where it is secured in position and notched with air vents 22 and similar to the tube 20.

The purpose of the above arrangement of the trough 23, holes 28, 29 and 20 and vent tubes 31 is to filter out any air bubbles which may develop in the fuel 11 which might affect or interfere with an accurate measurement of fuel quantity. Thus, in making the fuel 11 which gets into the tube 20 pass from one end of the trough across chamber 26 to the other end and into and through a length of the chamber 25 air bubbles therein will find escape through the vent tubes 31 and into the top of the tank 10 above the fuel level.

In order to adjust for temperature variations of the fuel 11 in the tank 10 a calibration device is employed. This device consists essentially of a signal reflector 32 located in a fixed position in the fuel 11 relative to a calibration transducer 14a. To this end the reflector 32 is mounted to the tank side wall 12 by an angle bracket 33 which may be attached by the same connectors 17 used to secure one of the conveyors 15. The transducer 14a, similar in all respects to each of the transducers 14, is mounted in any conventional manner to the external surface of the tank side wall 12 adjacent, and a known distance from, the reflector 32. Thus, the transducer 14a is employed to measure the velocity of propagation of the signal through the fuel 11 whereby temperature correction is accomplished.

OPERATION OF THE INVENTION

Referring more specifically to FIG. 1 the operation of the apparatus as above described is initiated by a microprocessor 34 which directs a stepper switch 35 to operatively connect a selected transducer 14. The microprocessor 34 then sends a signal to clear a counter 36 and thereafter supplies a timing pulse to a pulser 37 while simultaneously sending a signal to a sensitivity time control (STC) 38.

The pulser 37 provides a high voltage output which is supplied to the selected transducer 14. At the sme time the STC 38 sends a varying gain control voltage to a receiver 39 which reduces the gain of the receiver 39 at the begining of the ultrasonic signal flow through the fuel 11 being measured.

The selected transducer 14 generates an ultrasonic signal which travels through the conveyor 15 and into the tube 20. When the signal in the tube 20 reaches the fuel top surface, it returns to the selected transducer 14 which acts as an ultrasonic signal receiver generating an electrical voltage signal which is applied to the receiver 39.

When the high voltage signal was applied by the pulser 37 to the selected transducer 14 a signal was also applied to the receiver 39 (front end). This signal is passed as a start register signal to the counter 36. The electrical voltage signal from the selected transducer 14 which was applied to the receiver 39 is amplified thereby and applied to the counter 36 as a stop register signal. The counter 36 also receives a signal from a clock 40, preferably one with a stabile high frequency.

The time interval between the generated high voltage signal and the ultrasonically generated electrical voltage signal is registered within the counter 36 by the clock 40. This registered time interval represents the round trip propagation time within the fuel 11 being measured. The registered time interval is fed into and accepted within the microprocessor.

The above sequence is repeated by the stepping off of the switch 35 by the microprocessor 34 with each transducer 14. Periodically the switch 35 connects the calibration transducer 14a to the measuring circuit, as described above, and a propagation time measurement is made through the fuel 11 in the known distance between the transducer 14a and the reflector 32. This information is fed into and used by the microprocessor 34 to accurately calculate the fuel quantity over the range of fuel temperature.

Data from all of the transducers 14 is used to determine the fuel top surface plane by the microprocessor 34. Knowing the mathematical shape of the tank 10 and having the data from the calibration transducer 14a, the microprocessor 34 can calculate the quantity of fuel 11 in the tank 10. This quantity is then displayed on an indicator 41 visible to the operator or pilot of the aircraft.

I claim:

1. An ultrasonic quantity measuring apparatus for liquid in a container having a bottom and a known size and shape comprising:
    a source of ultrasonic energy located externally of said container;
    at least one conveyor within said container having low ultrasonic propagation loss properties with a stabile dielectric constant, said at least one conveyor being a rod essentially of a thermoset cross-linked styrene copolymer with a metallic coat;
    each said conveyor to direct the energy from said source located externally of said conveyor to a selected point adjacent the bottom of said container;
    a conduit extending from each said selected point substantially perpendicular to the top surface of the liquid in said container;
    an opening in each said conduit to permit liquid in said container to enter said conduit whereby said ultrasonic energy travels from said selected point through said conduit to the upper surface of said liquid where it is reflected back through said conduit;
    clock means to measure the time required for the ultrasonic energy travel aforesaid in each said conduit; and other
    means to receive each said time measurement from said clock means and to calculate the liquid quantity in said container therefrom and the known size and shape of said container.

2. An ultrasonic quantity measuring apparatus for liquid in a container having a bottom and a known size and shape comprising:
    a source of ultrasonic energy located externally of said container;
    at least one conveyor within said container having low ultrasonic propagation loss properties with a stabile dielectric constant, said at least one conveyor being a metal conduit filled with a low ultrasonic propagation loss material and closed at opposite ends by a polystyrene seal;
    each said conveyor to direct the energy from said source located externally of said container to a selected point adjacent the bottom of said container;
    a conduit extending from each said selected point substantially perpendicular to the top surface of the liquid in said container;
    an opening in each said conduit to permit liquid in said container to enter said conduit whereby said ultrasonic energy travels from said selected point through said conduit to the upper surface of said liquid where it is reflected back through said conduit;
    clock means to measure the time required for the ultrasonic energy travel aforesaid in each said conduit; and other
    means to receive each said time measurement from said clock means and to calculate the liquid quantity in said container therefrom and the known size and shape of said container.

3. The apparatus of claims 1 or 2 including an indicator connected to said other means to display the liquid quantity calculated thereby.

4. The apparatus of claims 1 or 2 including a filter associated with each said conduit to prevent air bubbles in the liquid from entering said conduit.

5. The apparatus of claim 4 wherein each said filter includes a trough completely enclosing the associated said conduit in the area of said selected point and said opening, at least one liquid vent hole in said trough adjacent the bottom thereof and remote from said conduit opening, and at least one vent tube from said trough extending from the top thereof to the top of said container.

6. The apparatus of claim 5 wherein said trough includes two adjacent chambers separated by a common center wall, said one liquid vent hole opens internally to one of said chambers, another said liquid vent hole pierces said common center wall remote from said one liquid vent hole, and said conduit opening opens into the other of said chambers remote from said another liquid vent hole.

7. The apparatus of claims 1 or 2 wherein said ultrasonic energy source includes a transducer associated with each said conveyor, a pulser connected to each said transducer, and means operative to apply a timing pulse to said pulser.

8. The apparatus of claim 7 wherein a plurality of said conveyors is employed and including a stepper switch connected between said transducers and said pulser, and a microprocessor for the programmed operation of said switch in a selected sequence.

9. The apparatus of claims 1 or 2 including a calibration device associated with said container liquid and operatively connected to said means to adjust for temperature variations of said liquid.

10. The apparatus of claim 9 wherein said calibration device includes a transducer to receive ultrasonic energy from said source, and a reflector located in a fixed position in said liquid at a predetermined distance from said transducer to receive and reflect signals therefrom.

11. The apparatus of claim 5 wherein said liquid container is a fuel tank adapted to be mounted in an airplane and a plurality of said conveyors is employed at selected locations in said tank and including a stepper switch operatively connected between each said conveyor and said energy source and means for the operation of said switch in a selected sequence.

12. The apparatus of claim 11 wherein said energy source includes a transducer associated with each said conveyor, a pulser connected to all said transducers, and a microprocessor operative to apply a timing pulse to said pulser, the stepper switch being connected between said transducers and said pulser.

13. The apparatus of claims 1 or 2 wherein said container is substantially rectangular and a plurality of said conveyors are employed with one conveyor being located proximate each corner of said container.

14. The apparatus of claim 13 including a calibration device mounted in said container adjacent the bottom thereof and operatively connected to said means to adjust for temperature variations of said liquid in said container.

15. The apparatus of claim 13 including a filter operatively connected to each said conduit adjacent said opening therein to prevent air bubbles in the liquid from entering said conduit.

16. The apparatus of claim 15 including at least one vent tube extending from the top of said filter to the top of said container.

* * * * *